United States Patent
Liu

(10) Patent No.: US 9,925,695 B2
(45) Date of Patent: Mar. 27, 2018

(54) POLY(LACTIC-CO-GLYCOLIC ACID (PLGA) COMPOSITES WITH MAGNESIUM WIRES ENHANCED NETWORKING OF PRIMARY NEURONS

(71) Applicant: The Regents of the University of California, Oakland, CA (US)

(72) Inventor: Huinan Liu, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/688,774

(22) Filed: Apr. 16, 2015

(65) Prior Publication Data

US 2016/0008516 A1 Jan. 14, 2016

Related U.S. Application Data

(60) Provisional application No. 61/980,187, filed on Apr. 16, 2014.

(51) Int. Cl.

| | |
|---|---|
| A61L 27/48 | (2006.01) |
| A61L 27/58 | (2006.01) |
| A61L 27/18 | (2006.01) |
| B29C 35/02 | (2006.01) |
| B29C 70/70 | (2006.01) |
| B29C 33/14 | (2006.01) |
| B29C 33/42 | (2006.01) |
| A61L 27/54 | (2006.01) |
| B29C 70/88 | (2006.01) |
| A61L 27/34 | (2006.01) |
| B29C 39/10 | (2006.01) |
| B29K 67/00 | (2006.01) |
| B29K 705/00 | (2006.01) |
| B29L 31/00 | (2006.01) |

(52) U.S. Cl.
CPC .............. *B29C 35/02* (2013.01); *A61L 27/18* (2013.01); *A61L 27/34* (2013.01); *A61L 27/58* (2013.01); *B29C 39/10* (2013.01); *A61L 2430/32* (2013.01); *B29C 70/70* (2013.01); *B29C 70/885* (2013.01); *B29K 2067/043* (2013.01); *B29K 2705/00* (2013.01); *B29K 2827/18* (2013.01); *B29L 2031/7532* (2013.01)

(58) Field of Classification Search
CPC ......... B29C 35/02; B29C 39/10; A61L 27/58; A61L 27/18; A61L 27/34
See application file for complete search history.

(56) References Cited

U.S. PATENT DOCUMENTS

| | | | | |
|---|---|---|---|---|
| 2004/0102793 | A1* | 5/2004 | Yaszemski | A61B 17/1128 606/152 |
| 2008/0220042 | A1* | 9/2008 | Hashi | A61K 38/58 514/1.1 |

FOREIGN PATENT DOCUMENTS

CN 102764454 * 11/2013

OTHER PUBLICATIONS

Ostrowski et al. Acta Biomaterialia, 2013, 9, 8704-8713.*
Zheng et al. CN 102764454, published: 2013, English language translation obtained on Oct. 16, 2016.*
S. Kehoe et al., "FDA approved guidance conduits and wraps for peripheral nerve injury: A view of materials and efficacy", Int. J. Care Injured 43 (2012), pp. 553-572.
Alexander R. Nectow et al., "Biomaterials for the Development of Peripheral Nerve Guidance Conduits," Tissue Engineering: Part B, vol. 18, No. 1, 2012, pp. 40-54.
Hung-Chuan Pan et al., "Magnesium supplement promotes sciatic nerve regeneration and down-regulates inflammatory response", Magnesium Research 2011: 24 (2): pp. 54-70.
Jeffrey M. Perlman, "Intervention Strategies for Neonatal Hypoxic-Ischemic Cerebral Injury," Clinical Therapeutics, vol. 28, No. 9, Sep. 2006, pp. 1353-1365.

* cited by examiner

*Primary Examiner* — Johann R Richter
*Assistant Examiner* — Genevieve S Alley
(74) *Attorney, Agent, or Firm* — Buchanan Ingersoll & Rooney PC

(57) ABSTRACT

A bioresorbable material incorporating magnesium (Mg) wires into NGCs is disclosed. The bioresorbable material includes magnesium, and a biodegradable polymer, for example, poly(lactic-co-glycolic acid (PLGA). The bioresorbable material can include magnesium wires incorporated into a poly(lactic-co-glycolic acid (PLGA) scaffold to provide both directional and biological cues in a fully bioresorbable material. A method of producing a bioresorbable material is also disclosed, which includes placing a plurality of magnesium (Mg) wires on a layer of a poly(lactic-co-glycolic acid (PLGA) solution, placing a second layer of the poly(lactic-co-glycolic acid (PLGA) solution on the plurality of magnesium (Mg) wires, and drying the plurality of magnesium (Mg) wires between the two layers of poly(lactic-co-glycolic acid (PLGA) solution.

19 Claims, 5 Drawing Sheets

POLY(LACTIC-CO-GLYCOLIC ACID) (PLGA) COMPOSITES WITH MAGNESIUM WIRES ENHANCED NETWORKING OF PRIMARY NEURONS

CROSS-REFERENCE TO RELATED APPLICATIONS

This application claims the benefit of U.S. Provisional Application No. 61/980,187, filed Apr. 16, 2014, the entire contents of which is hereby incorporated herein by reference.

TECHNICAL FIELD

The disclosure relates to incorporating magnesium (Mg) wires into nerve guidance conduits or channels ("NGCs"), and poly(lactic-co-glycolic acid) (PLGA) composites with magnesium wires enhanced networking of primary neurons.

BACKGROUND

Nerve injuries are among the most difficult injuries to heal because under normal physiological conditions, mature neurons do not undergo cell division. However, under certain conditions nerve fibers can regenerate across gaps. Injuries that result in long gaps can require surgical intervention, which may include the insertion of a nerve graft or guidance channel.

The current standard of care for surgical intervention in peripheral nerve injuries is the autologous graft. However, this procedure can present several drawbacks including additional surgery, size mismatch, possible neuropathy at the graft site, and the formation of painful neuromas. An alternative to grafting is the use of a nerve guidance channel (suture-able device that creates a channel connecting the distal and proximal ends of the damaged nerve).

Several nerve guidance channel (NGC) devices have been approved for clinical use by the FDA, but to date the majority of these devices have not been able to match the functional recovery of traditional nerve grafting procedures. These devices can be made of synthetic or natural polymers and may be resorbable or non-resorbable. The current generation of approved devices provides necessary passive support to injured nerves through entubulation, which can aid in physical guidance of outgrowing neurites and prevents ingrowth of fibrotic tissues. In designing improved NGCs, the goal is to incorporate biologically active factors that can provide additional cues and support in the hopes of achieving improved recovery.

Peripheral nerve regeneration follows a predictable pattern of four phases over several weeks. Briefly, upon injury, severed nerve stumps initiate repair by releasing a protein-rich exudate into the local environment. This exudate contains growth factors necessary for encouraging regeneration. In the second phase, a fibrin matrix can be established to link the distal and proximal nerve stumps. Fibroblasts migrate into the fibrin matrix from both stumps. In the subsequent phase shwann cells migrate along this matrix. By the second week axons begin to grow along in contact with shwann cells. In the final step to recovery, axons extend into the proximal stump and restore nerve connections, resulting in functional nerve recovery. An ideal NGC would be designed to take advantage of these phases. A further consideration is that to enhance regeneration, it is necessary to minimize the period of Wallerian degeneration (the process by which axonal segments that are severed distal to the soma of the cell break down and lose the ability to become electrically excited). The four main factors that govern Wallerian degeneration:

- Existence of shwann cells (which can guide axonal growth cone)
- Presence of growth factors that promote regeneration
- Presence of basal lamina
- The distal stump, which supplies neurotrophic factors to guide elongation of axonal growth cones coming from the proximal end.

Taking the physiology of nerve regeneration outlined above into account leads to a list of characteristics for the ideal NGC, in addition to the necessities of (i) mechanical support, (ii) linking nerve stumps, (iii) sequestering soluble factors, and (iv) preventing ingrowth of fibrotic tissue. These can include

- Flexible, bio-resorbable material to prevent nerve compression as the axon re-establishes connection in the NGC lumen
- Porosity to allow nutrient exchange
- Pre-loading with support cells to protect against Wallerian degeneration and speed up migration time
- Controlled release of chemical factors
- Inclusion of a provisional matrix that is biomimetic of basal lamina and oriented to discourage nerve outgrowth in undesired directions
- Intralumenal channels to mimic fasicular organization of nerve bundles
- Directional electrical activity to stimulate electrically active nerve cells

SUMMARY

A bioresorbable material is disclosed, the material includes magnesium; and a biodegradable polymer, and wherein the biodegradable polymer is poly(lactic-co-glycolic acid (PLGA).

A bioresorbable material is disclosed, the material comprising: at least one magnesium wire incorporated into a poly(lactic-co-glycolic acid (PLGA) scaffold to provide both directional and biological cues in a fully bioresorbable material.

A method of producing a bioresorbable material is disclosed, the method comprising: placing a plurality of magnesium (Mg) wires on a layer of a poly(lactic-co-glycolic acid (PLGA) solution; placing a second layer of the poly(lactic-co-glycolic acid (PLGA) solution on the plurality of magnesium (Mg) wires; and drying the plurality of magnesium (Mg) wires between the two layers of poly(lactic-co-glycolic acid (PLGA) solution.

DETAILED DESCRIPTION

Figure 1:
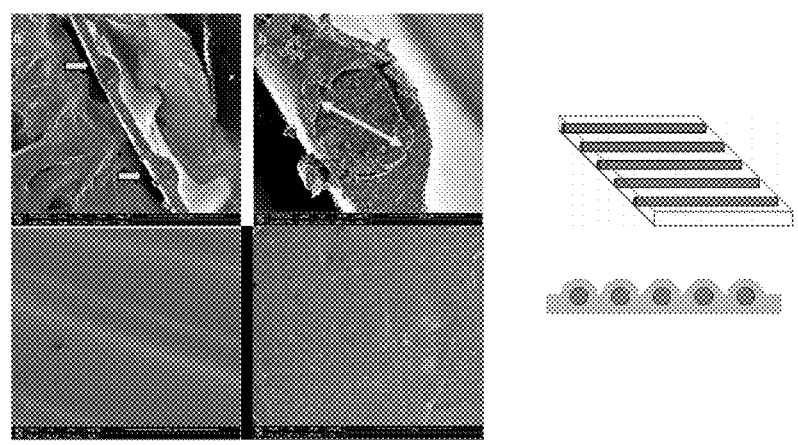
FIG. 1 are SEM micrographs of PLGA/Mg cross sections, which confirm full coverage of Mg wire (indicated by yellow arrow) within polymer, wherein (a) scale bar=500 µm (b) scale bar=100 µm, and along the top surface (c) sloping morphology covering Mg wires is seen, while the bottom surface (d) is flat and shows no topographical indications of wire location.

In accordance with an exemplary embodiment, in this disclosure a proposal of incorporating magnesium (Mg) wires into NGCs is disclosed for improving the functionality of nerve conduits. Mg is an attractive material for several reasons. For example, a bio-degradable metal, Mg will allow for creation of electrically active NGCs that are still fully biodegradable. In addition, Mg is necessary for many physiological processes, therefore Mg ions are naturally abundant and well tolerated in the body. However, one of the most compelling aspects of Mg for neural applications lies in its neuroprotective properties. Mg interacts with nerve cells by actively blocking one of the calcium ion channels, resulting in reduced excitability in the neuron. The medical profession has already found ways to take advantage of magnesium's neuroprotective properties. For example, application of Mg ions has been used as a nerve block during dental procedures and magnesium sulfate is a clinical treatment to prevent excitatory nerve damage in conditions ranging from eclampsia in pregnant women to ischemic stroke (Perlman, J. Clin Therapeutics. 2006; 28; 1353-65). Additionally, a recent in vivo study in mice reported that systemic delivery of Mg salts after sciatic nerve crush injury resulted in enhanced regeneration of the injured nerve (Pan, H. Mg Rsrch. 2011; 24; 54-70). Therefore, including Mg into NGCs is a facile method for providing means of electrical stimulation and controlled release of neuroprotective ions into a fully degradable conduit.

In this disclosure, poly(lactic-co-glycolic) acid (PLGA) is used as the base polymer for our NGC scaffold material. PLGA is a well-studied biodegradable synthetic polymer listed by the FDA as Generally Regarded As Safe (GRAS) and can be used in many implantable medical devices including NGCs. Mg will be incorporated into the polymer in the form of 125 μm diameter wire aligned parallel and equidistantly to one another in order to provide additional micro-topology to the conduit.

Materials and Methods:

Preparation of Magnesium Wire:

Prior to use, Magnesium (Mg) wires with a diameter of 125 μm (Goodfellow, Coraopolis Pa.) must be straightened to attain precise alignment. Straightening was achieved gravimetrically through suspension of lengths of wire in an oven with light weights affixed the end of each length, and annealing at 120° C. for 8 hours. Straightened wires were cut to the length necessary for use in scaffold creation (1 cm for PTFE mold method or 10 cm for rapid prototype method) then degreased and cleaned sequentially in acetone and ethanol under low-powered sonication for 30 min.

Scaffold Preparation Via PTFE Mold:

Thin films of PLGA and PLC were prepared using a solvent casting method in a PTFE mold. Either 100,000 MW 50:50 PLGA or 100,000 MW PCL (polymers acquired through PolySciTech, West Lafayette, Ind.) was dissolved in chloroform with 40° C. heat and sonication for an hour to create a 5% w/v solution. A base layer of polymer was cast, and then wires were placed at equidistant intervals within the mold. Each 1×1 cm scaffold contained 10 wires per cm. A second layer of polymer was cast on top of Mg wires, embedding wires completely between two layers of polymer. Scaffolds were dried in a chemical hood for 24 hours and under vacuum for an additional 48 hours to ensure complete removal of solvent. The 1×1 cm scaffolds were sterilized for 1 hour in 100% ethanol before cell culture.

Scaffold Preparation Via Rapid Prototype Mold:

To scale up scaffold production and improve wire alignment over longer wire segments, a mold was made through rapid prototyping. The mold was designed to be a negative of the final scaffold, and the design included grooves in which the wires are held to ensure equidistance and parallel alignment relative to each other.

A positive of the negative mold was designed in solid works and printed on a 3D printer using standard Acrylonitrile Butadiene Styrene (ABS) material. Rounded posts 500 μm tall by 500 μm wide and spaced at 500 μm intervals (maintaining the 10 wires per cm of PTFE fabricated scaffolds) span the length of the mold. A negative of the mold was cast in PDMS and this PDMS mold was used to prepare polymer scaffolds. PDMS swells in the presence of organic solvents, therefore acetone replaced chloroform as the solvent. To dissolve PLGA in acetone required increased heat and longer sonication time. Once polymer solutions were made, the same 2-phase solvent casting procedure was followed for fabrication as in PTFE mold.

Coating Conditions:

Sterilized PLGA scaffolds were and coated with poly-D-lysine (PDL) and laminin (Sigma-Aldrich, USA) before neural cell culture. These scaffolds did not undergo co-culturing procedures and will be denoted as "coated."

Culture Conditions:

Primary neurons were isolated from the hippocampi of prenatal mice (between E14 and E16) through digention with papain (Signa-Aldrigh, USA) and DNAse (Sigma-Aldrivh, USA) then seeded directly onto laminin+PDL coated scaffolds or glass coverslip controls (Bellco Glass) with an initial seeding density of 2 million per well of a 24 well plate (1.05 million cells/cm$^2$). Cells were maintained in complete media, Neurobasal Media+L-GLatamate+B-27 supplement (all culture media purchased through Life Technologies, USA). Media was replenished through half-exchanges every other day.

Co-Culture Conditions:

Primary astrocytes were isolated from the hippocampi of postnatal mice between 0.5 and 1.5 days old though digestion with 0.1% trypsin diluted in MEM media (Life Technologies, USA) then grown to confluency in DMEM media supplemented with 10% heat-inactivated fetal bovine serum (FBS). Confluent astrocyte cultures were trypsinized, seeded directly onto sterilized scaffolds through a cell strainer (to prevent clumping and ensure a uniform monolayer), and grown to confluency again. Primary neurons isolated as described above were seeded directly onto scaffolds covered with confluent astrocyte monolayer at a density of approximately 100 K and 150 K per well, for example, 135 K per well of a 24 well plate. Co-cultures were maintained in complete media, replenished through half-exchange every other day.

Immunostaining:

Coated scaffolds were fixed at eight and twelve days after seeding. Co-cultures were fixed at eight and fourteen days after seeding. All conditions were fixed in 4% paraformaldehyde (PFA). Coated scaffolds were stained with MAP2 (Sigma-Aldrich, USA) and counterstained DAPI (Life Technology). Co-cultured scaffolds were stained with MAP2 to show neurons, GFAP (VWR, USA) to show astrocytes and F-actin conjugated to phalloidin (Life Technologies) to show cell morphology. All scaffolds were mounted in vectashield with DAPI nuclear counter-stain (Vector labs).

Image Capture:

Images were taken on a Nikon Ti. Confocal stacks were collected on a Leica Sp5 inverted confocal microscope.

Image Analysis:

Confocal image stacks were converted to maximum intensity z-projections for analysis using the image processing software ImageJ. Tracing of neuron paths was performed using the filament tracer module for IMARIS software package (Bitplane). Quantification graphs were made using statistics calculated from neuron tracings.

Surface Characterization of PLGA/Mg Scaffold:

Scanning electron microscope (SEM) analysis of the scaffold surface shows that the Mg wires are completely embedded within the PLGA, leaving a smooth, relatively featureless surface. The bottom surface (FIG. 1D) shows striations from the machining of the Teflon mold. Cross sectional images (FIGS. 1a and 1b) clearly show the two distinct materials of the scaffold. Mg (noted by yellow arrows) has a granule morphology with fissures and observable grains, which is consistent with our labs observations for Mg. The polymer coating is approximately equal in thickness along the upper and lower surface of the scaffold, and the layer of polymer between wires has a thickness of between 100 μm and 125 μm. The interface between Mg and polymer is close with minimal gaping, indicating that air bubbles were not trapped during solvent casting.

Figure 2:
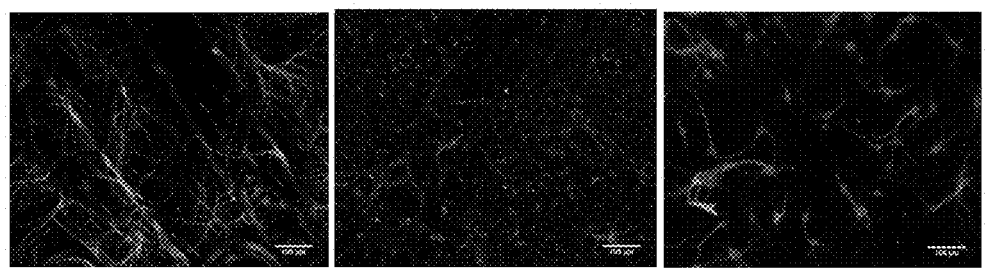
FIG. 2 are fluorescence images of PDL+Laminin Coated conditions: PLGA/Mg fixed after 8 days (a) and 12 days (b), and (c) Glass control fixed at 8 days, wherein all conditions stained with MAP2 (green) and DAPI (blue).

Primary Hippocampal Neuron Growth on Poly-D-Lysine (PDL)+Laminin Coated PLGA/Mg Composite Scaffolds:

The specific growth response for hippocampal neurons seeded onto PLGA/Mg scaffolds was investigated in order to determine if this composite material is cytocompatible and able to support dendritic outgrowth and survival. Glass cover slips were used as a reference because glass is known to be relatively inert, and previous disclosures in primary hippocampal cultures has established the compatibility of glass. The first round of experiments used a PDL/laminin pre-coating of scaffolds and glass coverslip controls because these proteins are necessary of hippocampal neuron survival in vitro. Fluorescence images (FIG. 2) show clear morphology differences between neurons gown on polymer/metal composite scaffolds as compared with glass controls. Neurons grown on scaffolds exhibit greater branching behavior and appear to form much denser dendritic network.

Figure 3:
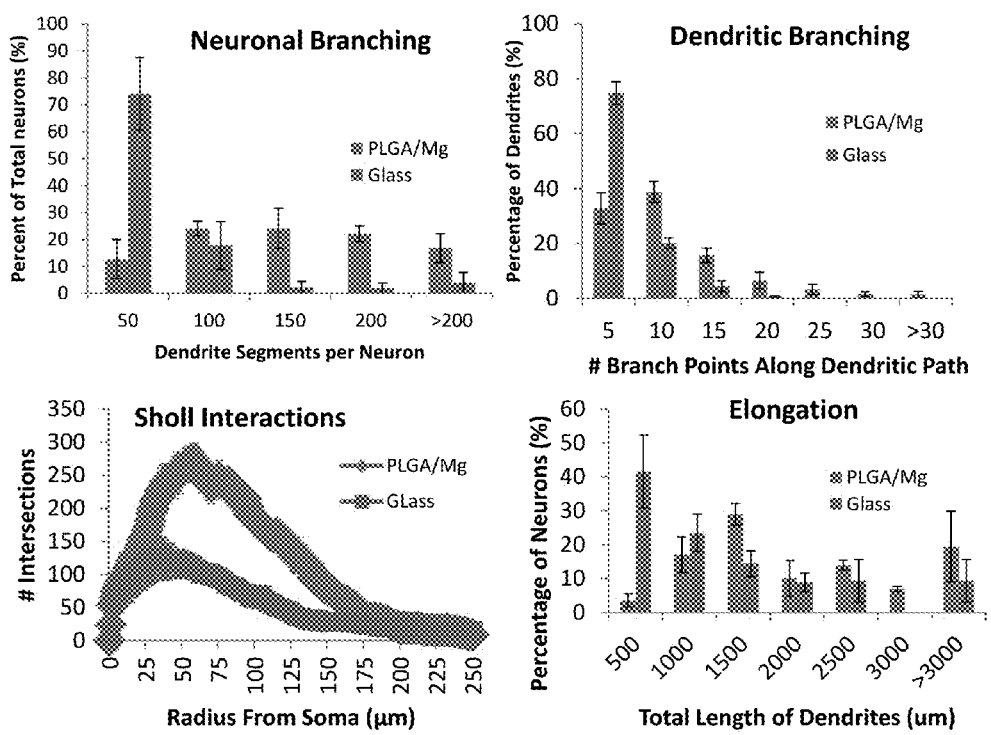
FIG. 3 illustrates network density panels in accordance with an exemplary embodiment.
Figure 4:
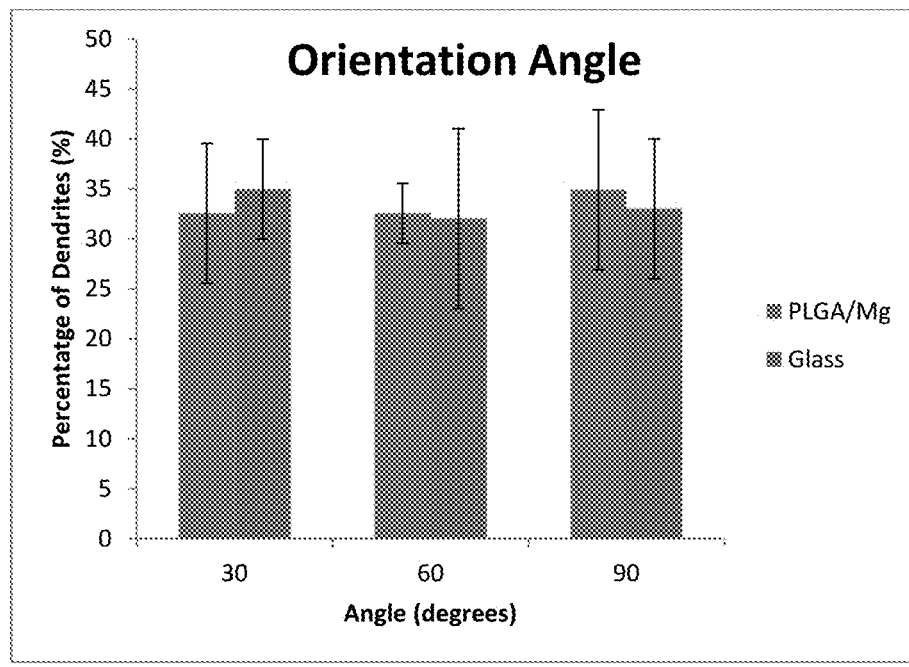
FIG. 4 illustrates orientation angle, wherein the angle between dendrite and wire, as measured on segments of images within a 40 μm radius of wires, for glass, angle measured with respect to x-axis.

To quantify these differences, tracing of the dendritic paths was performed using the Filament Tracer module of the IMARIS© software package (FIG. 3). In evaluating network density, four metrics were chosen: neuronal branching, dendritic branching, sholl interactions, and elongation. In addition to measuring networking, a cell density (Table 1) was examined.

TABLE 1

Neuronal Adhesion Density

| Material | Density (cells/cm$^2$) |
|---|---|
| PLGA/Mg | 54.8 ± 20.2 |
| Glass | 37.3 ± 22.8 |

Figure 5A:
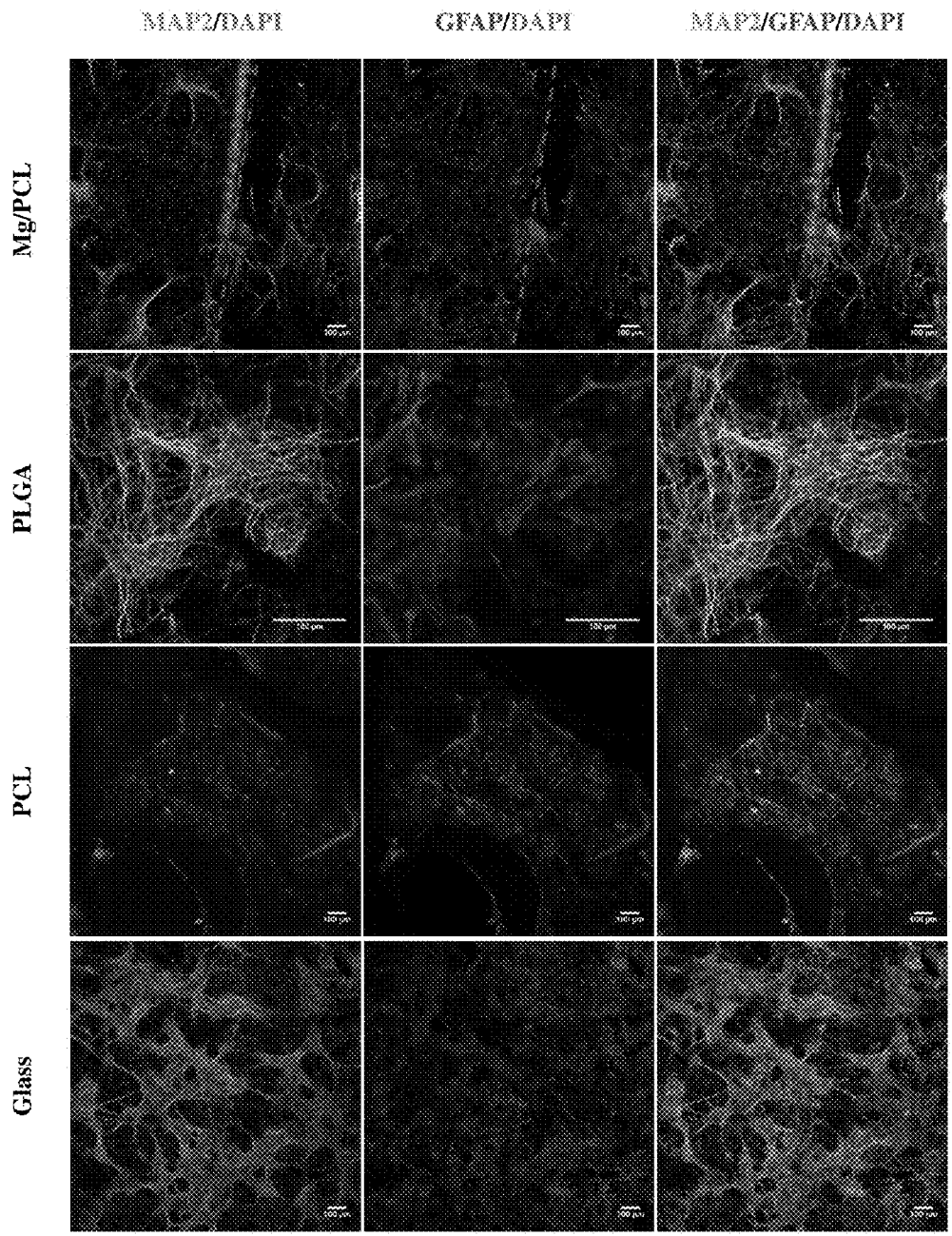
FIGS. 5A and 5B are fluorescence images of coculture, wherein panel A is fixed after 8 days of culture, and panel B is fixed after 14 days of culture
Figure 5B:
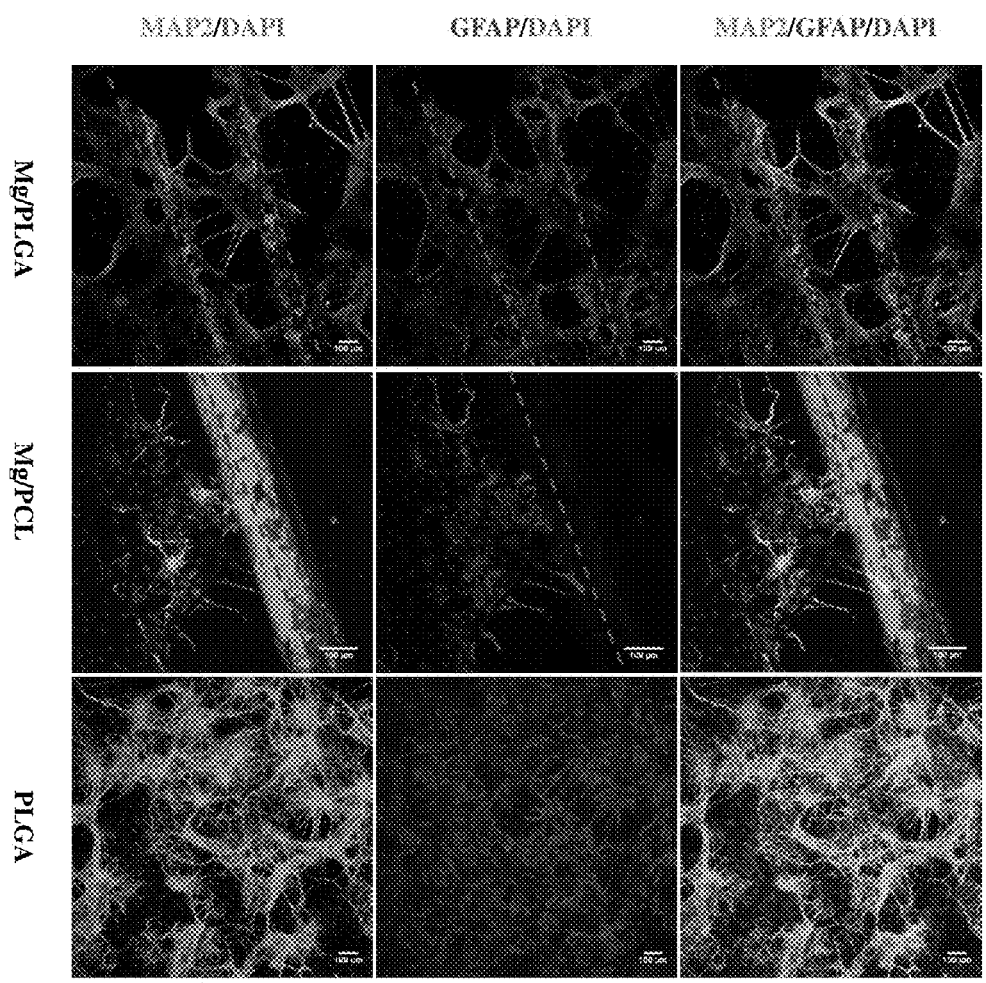

Finally, to evaluate the effectiveness of the Mg wires as topographical cues for directional elongation, the angle between dendritic segments and the wire axis (FIGS. 5A and 5B) were measured.

In accordance with an exemplary embodiment, the feasibility of incorporating Mg wires into biodegradable polymer scaffolds for neural applications is disclosed. Incorporating Mg into biomaterials for the nervous system can be attractive because Mg can be an important bioactive molecule used in hundreds of metabolic processes. Specifically of note in neural applications is the utility of Mg as a neuroprotective molecule that protects nerve cells from excitatory damage. However, the breakdown of bulk Mg in aqueous environments results in the creation of hydroxide ions, which may increase the alkalinity in the local environment, and Mg$^+$ ions, which will increase the local concentration of Mg. While Mg can be used clinically as a neuroprotectant, previous findings have shown that molar Mg concentration has an effect on cell morphology and proliferation of several different cell types.

In accordance with an exemplary embodiment, a study under co-culture conditions is disclosed, which can be an important proof-of-concept for future translation of this material, because it removes the reliance on pre-coating with isolated proteins. The co-culture condition can be a more bio-mimetic condition because in vivo the infiltration of support cells and deposition of a fibrin matrix are prerequisites for neuronal elongation.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method of producing a sheet of a bioresorbable material, the method comprising:
    arranging a plurality of spaced apart magnesium (Mg) wires in a planar arrangement on a first layer of a poly(lactic-co-glycolic acid) (PLGA) solution; and
    casting a second layer of the poly(lactic-co-glycolic acid) (PLGA) solution on the plurality of magnesium (Mg) wires and the first layer of the poly(lactic-co-glycolic acid) (PLGA) solution.

2. The method of claim 1, comprising:
    placing the plurality of spaced apart magnesium (Mg) wires and the poly(lactic-co-glycolic acid) (PLGA) solution in a mold.

3. The method of claim 2, wherein the mold is a PTFE mold.

4. The method of claim 3, comprising:
    placing grooves in the PTFE mold to ensure that each of the plurality of spaced apart magnesium (Mg) wires is equidistance and a parallel alignment of the plurality of spaced apart magnesium (Mg) wires is obtained.

5. The method of claim 1, comprising:
    straightening each of the plurality of spaced apart magnesium (Mg) wires before arranging the wires on the first layer of the poly(lactic-co-glycolic acid) (PLGA) solution.

6. The method of claim 1, comprising:
    arranging the plurality of spaced apart magnesium (Mg) wires at equidistant intervals.

7. The method of claim 1, comprising:
    embedding the plurality of spaced apart magnesium (Mg) wires completely within the first and the second layers of poly(lactic-co-glycolic acid) (PLGA), which form one or more scaffolds.

8. The method of claim 7, comprising:
drying the plurality of spaced apart magnesium (Mg) wires embedded within the first and the second layers of poly(lactic-co-glycolic acid) (PLGA) in a chemical hood and under vacuum to ensure complete removal of solvent.

9. The method of claim 8, comprising:
sterilizing the one or more scaffolds for 1 hour in 100% ethanol before cell culture.

10. The method of claim 9, comprising:
coating the sterilized PLGA scaffolds with poly-D-lysine (PDL) and laminin before neural cell culture.

11. The method of claim 1, wherein each of the plurality of spaced apart magnesium (Mg) wires has a diameter of about 125 μm.

12. The method of claim 1, comprising:
spacing the plurality of spaced apart magnesium (Mg) wires at 500 μm intervals.

13. A method of producing a sheet of a bioresorbable material, the method comprising:
arranging a plurality of spaced apart magnesium (Mg) based wires in a planar arrangement on a first layer of a biodegradable polymer; and
casting a second layer of another biodegradable polymer on the plurality of magnesium (Mg) based wires and the first layer of the biodegradable polymer.

14. The method of claim 13, comprising:
drying the plurality of spaced apart magnesium (Mg) based wires embedded within the first and second layers of biodegradable polymer in a chemical hood and under vacuum to ensure complete removal of solvent.

15. The method of claim 13, comprising:
arranging the plurality of spaced apart magnesium (Mg) based wires at equidistant intervals.

16. The method of claim 13, comprising:
embedding the plurality of spaced apart magnesium (Mg) based wires completely within the first and the second layers of biodegradable polymers, which form one or more scaffolds.

17. The method of claim 16, comprising:
coating the one or more scaffolds composed of two layers of biodegradable polymers and one layer of spaced apart magnesium (Mg) based wires with poly-D-lysine (PDL) and laminin before neural cell culture.

18. The method of claim 13, comprising:
placing the plurality of spaced apart magnesium (Mg) based wires and the biodegradable polymer in a mold; and
placing grooves in the mold to ensure that each of the plurality of spaced apart magnesium (Mg) based wires is equidistance and a parallel alignment of the plurality of spaced apart magnesium (Mg) based wires is obtained.

19. A bioresorbable material prepared by the method of claim 1.

* * * * *